United States Patent
Mayan Santos et al.

(10) Patent No.: US 10,213,481 B2
(45) Date of Patent: Feb. 26, 2019

(54) COMPOSITIONS AND METHODS TO TREAT INFLAMMATORY JOINT DISEASE

(71) Applicant: Rowan University, Glassboro, NJ (US)

(72) Inventors: Maria D. Mayan Santos, Perillo Oleiros (ES); Francisco J. Blanco Garcia, Oleiros (ES); Paula Carpintero Fernandez, A Coruna (ES); Gary S. Goldberg, Voorhees, NJ (US)

( * ) Notice: Subject to any disclaimer, the term of this patent is extended or adjusted under 35 U.S.C. 154(b) by 167 days.

(21) Appl. No.: 14/902,502

(22) PCT Filed: Jul. 2, 2014

(86) PCT No.: PCT/US2014/045229
§ 371 (c)(1),
(2) Date: Dec. 31, 2015

(87) PCT Pub. No.: WO2015/003049
PCT Pub. Date: Jan. 8, 2015

(65) Prior Publication Data
US 2016/0375096 A1 Dec. 29, 2016

Related U.S. Application Data

(60) Provisional application No. 61/842,195, filed on Jul. 2, 2013.

(51) Int. Cl.
| | | |
|---|---|---|
| A61K 38/16 | (2006.01) |
| C07K 14/42 | (2006.01) |
| A61K 36/185 | (2006.01) |
| A61K 36/48 | (2006.01) |
| A61K 45/06 | (2006.01) |
| A61K 38/17 | (2006.01) |
| G01N 33/68 | (2006.01) |
| A61K 39/395 | (2006.01) |
| C07K 16/18 | (2006.01) |
| C07K 16/40 | (2006.01) |

(52) U.S. Cl.
CPC .......... *A61K 38/168* (2013.01); *A61K 36/185* (2013.01); *A61K 36/48* (2013.01); *A61K 38/1732* (2013.01); *A61K 38/1735* (2013.01); *A61K 39/3955* (2013.01); *A61K 45/06* (2013.01); *C07K 14/42* (2013.01); *C07K 16/18* (2013.01); *C07K 16/40* (2013.01); *G01N 33/6893* (2013.01); *C07K 2317/76* (2013.01); *G01N 2800/102* (2013.01)

(58) Field of Classification Search
None
See application file for complete search history.

(56) References Cited

FOREIGN PATENT DOCUMENTS

| WO | WO 2004/026909 | * | 4/2004 |
| WO | WO-2004026909 A2 | * | 4/2004 | ............ A61K 31/70 |

OTHER PUBLICATIONS

Ekwall et al., Arthritis Res. Ther., 2011, vol. 13(2):R40.*
Ochoa-Alvarez et al., PLoS One, 2012, vol. 7(7): e41845, Epub. 2012, Jul. 23.*
Cronstein, B.N., Pharmacol. Rev., 2005, vol. 57(2):163-172.*

* cited by examiner

*Primary Examiner* — Xiaozhen Xie
(74) *Attorney, Agent, or Firm* — Saul Ewing Arnstein & Lehr LLP; Doningos J. Silva

(57) ABSTRACT

The present invention provides pharmaceutical compositions and methods to treat inflammatory joint diseases and decrease cartilage degradation. In certain embodiments, the pharmaceutical compositions of the invention comprise an agent that binds to a α-2,3-sialic acid transmembrane glycoprotein.

18 Claims, 6 Drawing Sheets
Specification includes a Sequence Listing.

a b

COMPOSITIONS AND METHODS TO TREAT INFLAMMATORY JOINT DISEASE

CROSS-REFERENCE TO RELATED APPLICATION

This application is a 35 U.S.C. § 371 national phase application from, and claims priority to, International Application No. PCT/US2014/045229, filed Jul. 2, 2014, and published under PCT Article 21(2) in English, which claims priority of U.S. Provisional Application No. 61/842,195, filed Jul. 2, 2013, the contents of all of which applications are incorporated herein by reference in their entireties.

FIELD OF THE INVENTION

The invention relates to pharmaceutical compositions, and methods for treating inflammatory joint disease.

BACKGROUND OF THE INVENTION

This invention relates to pharmaceutical compositions comprising an agent that binds to α-2,3-sialic acid transmembrane glycoproteins and methods of using these pharmaceutical compositions for treating joint inflammatory disease, as well as methods for preventing the degradation of cartilage.

Joint inflammatory disease can be characterized as inflammation of the joint that may cause pain, stiffness, and some redness of the skin about the joint, and can be a result of an infection, physical injury, autoimmune disease or a type of arthritis. Effusion of fluid into the joint cavity is common, and examination of this fluid is often a valuable procedure for determining the nature of the disease. The inflammation may be of such a nature and of such severity as to destroy the joint cartilage and underlying bone and cause irreparable deformities. Adhesions between the articulating members are frequent in such cases, and the resulting fusion with loss of mobility is called ankylosis. Inflammation restricted to the lining of a joint (the synovial membrane) is referred to as synovitis. Rheumatoid arthritis (RA) is an autoimmune disease that results in a chronic, systemic inflammatory disorder that principally attacks flexible (synovial) joints. Experimental data suggest that cases of arthritis can exhibit a notable increase in levels of reactive oxygen species (ROS) and proinflammatory cytokines. This process is likely to be pronounced during periods of arthritic flares, and triggers a characteristic degradation of cartilage matrix.

Arthritis is characterized by degradation of the chondrocyte extracellular matrix (ECM), which results in articular cartilage erosion. Susceptibility of articular cartilage to arthritic degradation is associated with posttranslational modifications of ECM proteins. Glycosylation is the most common posttranslational modification of cell surface and ECM proteins. As a result, chondrocytes carry a dense coat of carbohydrates on their surfaces. These carbohydrate moieties mediate a wide variety of cell-cell and cell-matrix interactions that are critical for bone development and function. Current treatments for Arthritis consist mostly of anti-inflammatory and immunosuppressant medications. Unfortunately, these approaches are only modestly effective to ameliorate symptoms, and may cause significant side effects including increased risk of viral infection and cancer. Therefore there is a need for new pharmaceutical compositions and methods to treat arthritis.

SUMMARY OF THE INVENTION

At least one aspect of the invention is directed to methods of reducing cartilage degradation comprising administering to a subject in need thereof a therapeutically effective amount of a pharmaceutical composition comprising an agent that binds to a α-2,3-sialic acid transmembrane glycoprotein and a pharmaceutically acceptable carrier. These agents include antibodies, selectins, mucins, galectins, and lectins including without limitation lectin derived from *Maackia amurensis* seed (MASL).

Another aspect of the present invention is directed to methods of treating a patient suffering from an inflammatory joint disease or is at risk of developing such condition comprising administering said subject a therapeutically effective amount of a pharmaceutical composition comprising an agent that binds to a α-2,3-sialic acid transmembrane glycoprotein and a pharmaceutically accepted carrier.

In at least one embodiment, such transmembrane glycoprotein is Podoplanin (PDPN). In yet another embodiment, the agent is MASL or viscumin.

Another aspect of the present invention is directed to methods for screening a subject for an inflammatory joint disease comprising assessing the level of expression of PDPN in a subject. In one embodiment such method of screening follows the steps of (a) administering to a subject the pharmaceutical composition containing an agent that binds to PDPN, wherein the agent carries a detectable label, (b) measuring the level of the detectable label present in the subject, (c) comparing the measured level with a baseline obtained from the subject or normalized level of a control subject that is not suffering from inflammatory joint condition, wherein a deviation of the level from the baseline is an indication of inflammatory joint disease; and wherein the deviation is caused by a modification of a PDPN sialylated expression pattern on a chondrocyte.

Another aspect of the present invention is directed to methods for screening the susceptibility of a subject suffering from an inflammatory joint disease in need of chondrocyte PDPN inhibition treatment comprising (a) obtaining chondrocytes from a subject, (b) measuring the chondrocyte expression level of PDPN, (c) administering an agent that binds to PDPN, (d) optionally detecting ROS production, (e) comparing the measured level with a baseline obtained from the subject or normalized level of a control subject that is not suffering from inflammatory joint disease, wherein a deviation of the level from the baseline is an indication of inflammatory joint disease; and wherein the deviation is caused by a modification of an expression pattern of PDPN and/or ROS levels.

Another aspect of the present invention is directed to pharmaceutical compositions that comprise an arthritic effective amount of an agent that binds to a α-2,3-sialic acid transmembrane glycoprotein and a pharmaceutically acceptable carrier. In one embodiment, such agent is a lectin, an antibody or a combination thereof. In another embodiment, the lectin is obtained from the plant genus of *Maackia* or *Viscum*. In another embodiment, the lectin is *Maackia amurensis* seed lectin (MASL).

In another embodiment, the pharmaceutical compositions of the present invention are in the form of oral, topical or injectable dosage forms. In yet another embodiment, the composition further contains a second active agent selected from the group consisting of NSAIDs, corticosteroids, opiate agonists, TNF inhibitors, and DMARDs.

Another aspect of the present invention is directed to kits for detecting an expression level of PDPN in a chondrocyte comprising an agent that targets PDPN.

BRIEF DESCRIPTION OF THE FIGURES

FIG. 1A shows that oligomycin increased the production of α-2,3-sialylatated glycoproteins in cartilage explants as detected by MASL binding. FIGS. 1B and 1C show that oligomycin treatment increased the expression of enzymes responsible of ECM degradation of ECM including matrix metalloproteinase 3 (MMP3) and matrix metalloproteinase 13 (MMP13) in primary chondrocyte cell cultures and cartilage explants. FIG. 1C shows that effects of this treatment were evident after 7 days when explants showed increased ECM degradation observed by a significant increase in the size of lacunas and positive staining for MMP3 and MMP13 from lacunas to the matrix. FIG. 1D shows that oligomycin treatment increased ROS production in chondrocytes by over 10 fold. FIGS. 1D and 1E show that established (Tc28a2) and primary chondrocytes pretreated with MASL were effectively protected from ROS production in the face of oligomycin treatment. FIG. 1F shows that induction of inflammatory cytokines including IL-6 and COX2 by olygomycin was also suppressed by treatment with nanomolar MASL concentrations.

FIG. 2A shows that oligomycin treatment decreased safranin uptake and disrupted the cartilage ECM as evidenced by ulcerations and increasing lacunas size. However, MASL prevented this cartilage destruction and reduced ECM degradation detected by safranin uptake. FIGS. 2B and 2C show that gene expression analysis and IHC assays revealed that MASL suppressed COX2, MMP3 and MMP13 induction by oligomycin treatment

DETAILED DESCRIPTION OF THE INVENTION

Figure 1A:
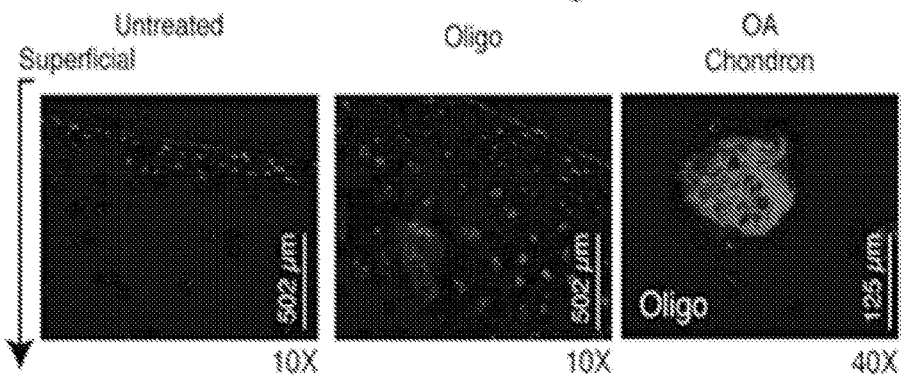
FIGS. 1A-1F are a set of diagrams showing that MASL inhibits matrix metalloproteinase, reactive oxygen species (ROS), and inflammatory cytokines induced by oligomycin.
Figure 1B:
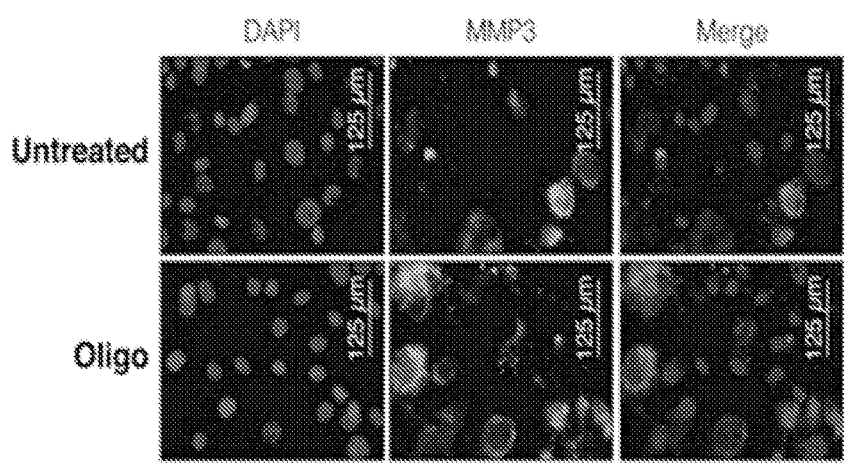
Figure 1C:
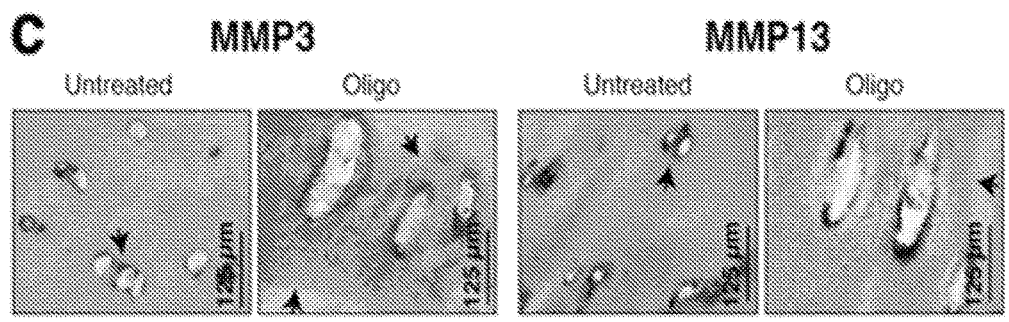
Figure 1D:
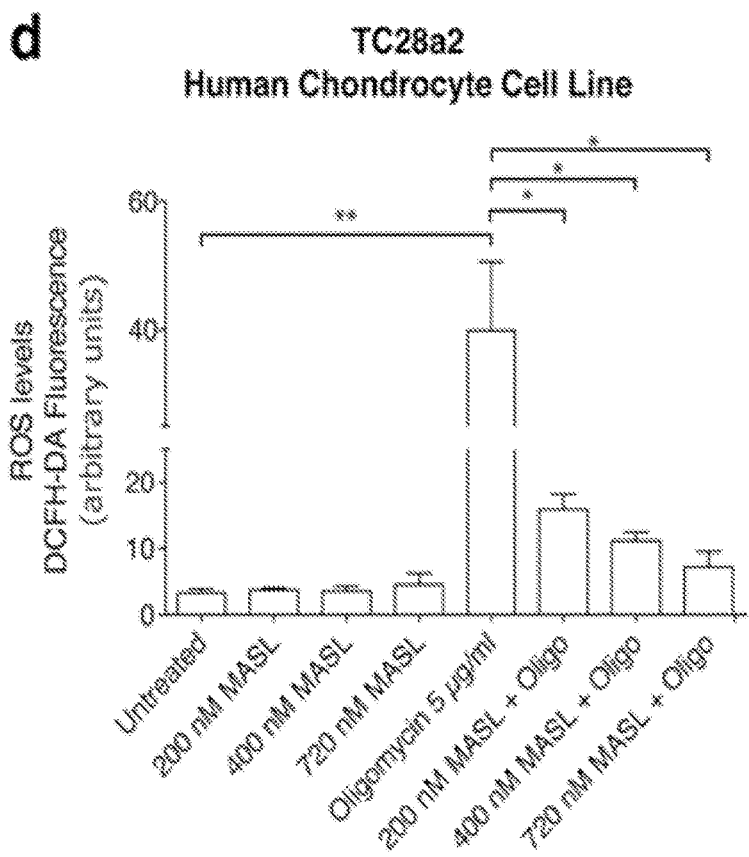
Figure 1E:
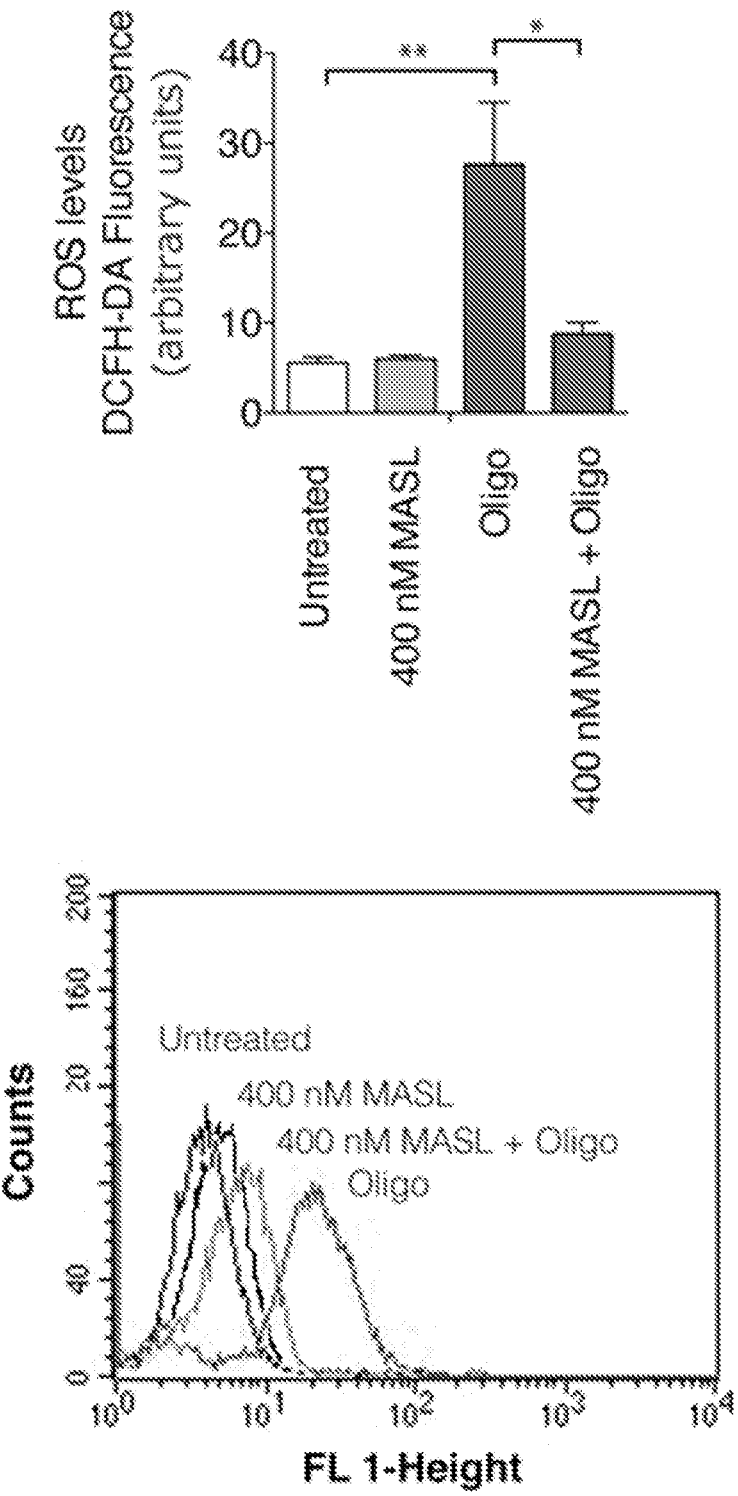
Figure 1F:
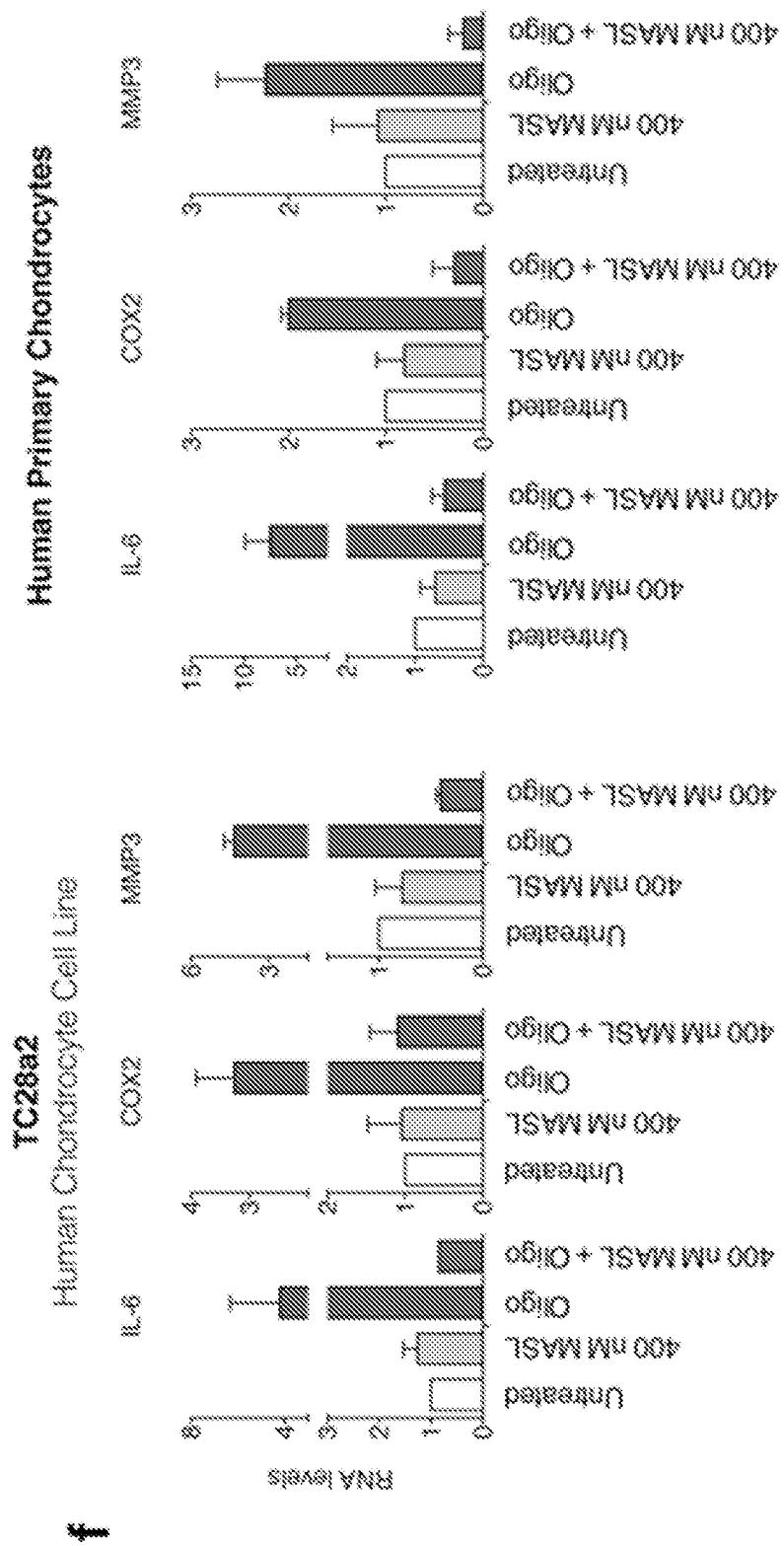

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. All publications and patents referred to herein are incorporated by reference in their entirety. As such to facilitate an understanding of the present invention, a number of terms and phrases are defined below:

As used herein, the term "antibody" refers to an immunoglobulin or antigen-binding fragment thereof, and encompasses any such polypeptide comprising an antigen-binding fragment of an antibody. In a preferred embodiment, the antibody targets and binds to at least a portion of the extracellular domain of PDPN expressed on a chondrocyte membrane. The term includes but is not limited to polyclonal, monoclonal, monospecific, polyspecific, humanized, human, single-chain, single-domain, chimeric, synthetic, recombinant, hybrid, mutated, grafted, and in vitro generated antibodies. The term "antibody" also includes antigen-binding fragments of an antibody. Examples of antigen-binding fragments include, but are not limited to, Fab fragments (consisting of the VL, VH, CL and CH1 domains); Fd fragments (consisting of the VH and CH1 domains); Fv fragments (referring to a dimer of one heavy and one light chain variable domain in tight, non-covalent association); dAb fragments (consisting of a VH domain); single domain fragments (VH domain, VL domain, VHH domain, or VNAR domain); isolated CDR regions; (Fab')2 fragments, bivalent fragments (comprising two Fab fragments linked by a disulphide bridge at the hinge region), scFv (referring to a fusion of the VL and VH domains, linked together with a short linker), and other antibody fragments that retain antigen-binding function.

The term "baseline" as used herein refers to the level of a biomarker in a normal subject without arthritis.

An "isolated polypeptide" refers to a polypeptide that has been separated from other proteins, lipids, and nucleic acids with which it is naturally associated. The term polypeptide may be used interchangeably with the term "protein". The polypeptide constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods, which may include synthetic or unnatural amino acids, for example D-amino Acids. A functional equivalent of MASL refers to a polypeptide derivative of MASL, e.g., a protein having one or more point mutations, insertions, deletions, truncations, a fusion protein, or a combination thereof. It retains substantially the activity of MASL, i.e., the ability to target and bind to a α-2,3-sialic acid glycoprotein while having little or no toxic effect on other cells or organs in the body. The isolated polypeptides can contain functional fragments of MASL. In general, the functional equivalent is at least 75% (e.g., any number between 75% and 100%, inclusive, e.g., 70%, 80%, 85%, 90%, 95%, and 99%) identical to the amino acid sequences of MASL.

As used herein, the term "label" refers to a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}I$, $^{131}I$, $^{35}S$, $^{3}H$ or P), enzymes (e.g., alkaline phosphatase, horseradish peroxidase, luciferase, or β-glactosidase), fluorescent moieties or proteins (e.g., fluorescein, rhodamine, phycoerythrin, Green Flourescent Protein (GFP), or Blue Fluorescent Protein (BFP)), or luminescent moieties (e.g., Qdot™ nanoparticles by the Quantum Dot Corporation, Palo Alto, Calif.).

As used herein, Reactive Oxidative Species or ROS refer to reactive moieties such as hydroxyl radicals (OH.), ionic species such as superoxide anions ($O_2^-$), and neutral but highly reactive oxidizing molecules such hydrogen peroxides ($H_2O_2$).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue is preferably replaced with another amino acid residue from the same side chain family, including synthetic or unnatural amino acids, for example D-amino Acids. Alternatively, mutations can be introduced randomly along all or part of MASL, such as by saturation mutagenesis, and the resultant mutants can be screened for the ability to improve the ocular condition and/or to identify mutants that retain the activity as described below in the examples.

"Subject in need thereof" as used herein refers to a subject that has been diagnosed with an inflammatory joint disease, exhibits symptoms of an inflammatory joint disease, and/or at risk of an inflammatory joint disease because of a genetic predisposition, age, physical injury, or lifestyle that results in a constant pressure or force on a joint, for example a person that jogs on a daily basis that would result in constant force amount of force on the knee joints.

"Substantially identical" as used herein refers to that the nucleic or amino acid sequence is at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence. Preferably, such variant nucleic acid and polypeptide sequences will share 75% or more (i.e. 80, 85, 90, 95, 97, 98, 99% or more) sequence identity with the sequences referred to in the application.

The term "therapeutically effective amount," as used herein, pertains to that amount of an active compound, or a material, composition or dosage form comprising an active compound, which is effective for producing the desired therapeutic effect, commensurate with a reasonable benefit/risk ratio to avoid excess concentration of such drugs to the extent that it would neutralize its expected therapeutic effects or cause undesirable cell damage.

The term "treatment" or "therapy" as used herein in the context of treating a condition to the extent that a positive clinical benefit is observed. Thus, a course of therapy includes prophylactic treatment, and further pertains generally to the therapy of a human subject. Treatment includes combination treatments and therapies, in which two or more treatments or therapies modalities are combined, for example, sequentially or simultaneously. Examples of treatments and therapies include, but are not limited to, lectin therapy with or without the use of other active compounds, surgery and/or other drug treatments generally known to inflammatory joint diseases.

This present invention relates to pharmaceutical compositions comprising an agent that binds to α-2,3-sialic acid transmembrane glycoproteins and methods of using these pharmaceutical compositions for treating joint inflammatory disease. Another aspect of the present invention is directed to methods for prophylactically treating or preventing the degradation of joint cartilage. At least one aspect of the present invention is directed to the use of lectins for treatment of arthritis. In one embodiment, lectins are described that are capable of binding to specific carbohydrate moieties associated with transmembrane structure such as α-2,3-sialic acids. In at least one aspect of the invention, such lectin includes those that are derived from plants such as *Maackia* and *Viscum*. For example, lectin from the *Maackia amurensis* seed (MASL), binds to α-2,3-sialic acid glycoproteins.

At least one aspect of the present invention relates to the discovery that Podoplanin (PDPN), a α-2,3-siallylated transmembrane mucin receptor protein, is induced in cartilage of osteoarthritic patients. In fact, it is discovered that such PDPN induction causes cartilage breakdown. In at least one embodiment, the present inventors for the first time provide methods of reversing PDPN induction in cartilage tissues at risk. In one method, lectin containing compositions are described that can limit or reverse PDPN induction in cartilage tissues.

At least one aspect of the present invention is directed to methods of prophylactically treating or preventing cartilage breakdown initiated by ROS, inflammatory cytokines, and metalloproteinases. In one embodiment, the therapeutic amount of the agent achieves nanomolar concentrations of MASL in the region of interest so that MASL binds to PDPN, the chondrocytes are protected against cartilage breakdown, while the viability of the cells exposed are not compromised.

In one embodiment, the present invention is directed to a pharmaceutical composition comprising an agent that binds to α-2,3-sialic acid transmembrane glycoproteins in a pharmaceutically acceptable carrier. In another embodiment, the agent that binds to α-2,3-sialic acid transmembrane glycoprotein targets the expression of such glycoprotein in chondrocytes and/or on the surface of chondrocytes. In yet another embodiment, the α-2,3-sialic acid transmembrane glycoprotein is PDPN. In yet another embodiment, agents that bind to PDPN include such compounds as PDPN agonists, PDPN antagonists, natural agents that bind to PDPN such as lectin, selectin, mucin, galactin, or an antibody specific to PDPN, and/or the extracellular domain of PDPN. In a further embodiment, the agent may be conjugated to a detectable label.

In an embodiment, the lectin may be a plant derived lectin, such as *Macckia amurensis, Maackia australis, Maackia chekiangensis, Maackia ellipticocarpa, Maakia fauriei, Macckia floribunda, Maakia hugehesis, Maackia hwashanensis, Maackia tashiroi*, and *Maackia tenuifolia*. In a preferred embodiment the lectin is derived from *Maackia amurensis* seed (MASL), and may include without limitation, two isolectins hemagglutinin (MAH) and leukoagglutinin (MAL). In yet another embodiment, lectin is derived from *Viscum* plant such as *Viscus album*. In yet another embodiment, the lectin is viscumin.

MAH preferentially binds to an O-linked, disialylated tetrasaccharide with the structure Siaα2-3Galβ1-3 (Neu5Acα2-6)GalNAc, in which the α2-6-linked Neu5Ac is not required for binding. One with ordinary skill in the art may make recombinant MASL using the amino acid sequences for MAL and MAH that are described in Yamamoto et al., *J Biochem* (Tokyo) 1997; 121:756-761; Imberty et al., *J Biol Chem* 2000; 275: 17541-17548, and/or Ochoa-Alvarez et al., *PLoS One* 7:e41845. In one embodiment, mixtures of MAL and MAH, also referred to as MASL, are described for a new use by targeting and binding to α2-3 linked sialic acids on transmembrane glycoproteins in chondrocytes.

MASL may be manufactured by methods generally known in the art and further isolated for the presently claimed new use. Naturally occurring MASL, genetic engineered MASL, and chemically synthesized MASL can also be used for practicing the invention disclosed herein. In another embodiment, MASL may be obtained by recombinant DNA technology or may have the same amino acid sequence as naturally occurring MASL or a functionally equivalent thereof. In yet another embodiment, MASL is chemically modified including MASL subjected to conformational change, addition or deletion of a sugar chain, and MASL to which a compound such as polyethylene glycol has been bound. Once purified and tested by standard methods or according to the method described in the examples below, MASL can be included in a pharmaceutical composition.

The amino acid composition of the MASL described herein may vary without disrupting the ability to target and bind to a α-2,3-sialic acid transmembrane glycoprotein. In a preferred embodiment, MASL targets and binds to an α-2,3-sialic acid glycoprotein expressed by a chondrocyte. In a preferred embodiment MASL targets and binds to PDPN located on a chondrocyte membrane. For example, it can contain one or more conservative amino acid substitutions.

In another embodiment, methods of preparing MASL include isolating naturally occurring polypeptides or as recombinant polypeptides. In one aspect, to prepare recombinant polypeptides, a nucleic acid encoding it can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptides of this invention.

In another aspect, pharmaceutical composition for administration to a subject is described. It is preferable to formulate the molecules in a composition comprising one or more pharmaceutically acceptable carriers. The carrier may be formed of any suitable pharmaceutically acceptable or therapeutically acceptable material. In particular, the pharmaceutical composition of the invention can be formulated for systemic and local administration, for example a biodegradable controlled release polymeric matrix.

For systemic administration, the pharmaceutical composition of the present invention can be in the form of granules, discrete pellets or particles contained in a capsule, or particles embedded in a tablet or suspended in a liquid suspension. In a preferred embodiment, the pharmaceutical composition is formulated to provide a therapeutic concentration of MASL at the region of interest. In one embodiment, the concentration of MASL at the local levels such as a joint, connective tissues, or a location near cartilage is in the range of 50 nM to about 2800 nM. The term “local level” of a joint refers to the area surrounding a joint of interest, including the cartilage, synovial membrane, synovial cavity, ligaments, tendons, meniscus and bursas.

In an embodiment of the present invention, the pharmaceutical composition contains a modified release component. Such component can be in the form of a modified release particle, coating, layer, or matrix. By “modified release”, it is meant that the component allows for a release of an active compound (MASL) from the component that is (immediate or) not immediate. For example, the release may be controlled or it may be delayed in part and immediate in other parts. By “controlled release” it is meant that the release of the compound is characterized by a specific release profile in which, for a specific period of time, a specific rate of release is achieved. Various different rates of release may be achieved at different periods of time. By “delayed release” it is meant that the compound is released after a period of delay in which the compound is not released. The compound may be released immediately following the period of delay, in which case the component is considered to be a “delayed immediate release” either in a particle or a layer or alike. Alternatively, the compound may be released on a controlled release basis following the initial delay period, in which case the particle is considered to be a “delayed controlled release” particle. In a further embodiment, the pharmaceutical composition may contain a binder, an excipient, lubricant, disintegrator, and a wetting agent.

To allow for modified release of the compound of interest (MASL), the particle may contain a modified release coating or a modified release matrix. The coating or matrix serves to retard the release of the compound from the particle. The release characteristics of a particle may be adjusted by adjusting the amount of the coating or matrix, for example, by applying a thicker coating to the particle, or by adjusting the ingredients of the coating or matrix.

Any coating material which modifies the release of the compound of interest (MASL) in the desired manner may be used. Examples of coating materials which are suitable for use in the practice of the present invention include: polymer coating materials, such as cellulose acetate phthalate, cellulose acetate trimaletate, hydroxy propyl methylcellulose phthalate, polyvinyl acetate phthalate, ammonio methacrylate copolymers such as those sold under the trademark EUDRAGIT® RS and RL, poly acrylic acid and poly acrylate and methacrylate copolymers such as those sold under the trademark EUDRAGIT® S and L, polyvinyl acetaldiethylamino acetate, hydroxypropyl methylcellulose acetate succinate, and shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydoxypropyl cellulose, hydroxypropylmethylcellulose (HPMC), polyvinylpyrrolidone, crosslinked starch, microcrystalline cellulose, chitin, aminoacryl-methacrylate copolymer (EUDRAGIT® RS-PM, Rohm & Haas), pullulan, collagen, casein, agar, gum arabic, sodium carboxymethyl cellulose, (swellable hydrophilic polymers) poly(hydroxyalkyl methacrylate), polyvinylpyrrolidone, anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. about 30 k-300 k), polysaccharides such as agar, acacia, karaya, tragacanth, algins and guar, polyacrylamides, AQUAKEEP® acrylate polymers, diesters of polyglucan, crosslinked polyvinyl alcohol and poly N-vinyl-2-pyrrolidone, sodium starch glucolate; hydrophilic polymers such as polysaccharides, methyl cellulose, sodium or calcium carboxymethyl cellulose, nitro cellulose, carboxymethyl cellulose, cellulose ethers, polyethylene oxides (e.g. POLYOX®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. EUDRAGIT®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate. Suitable solvents include acetone and isopropyl alcohol.

Any matrix material which modifies the release of the compound of interest (MASL) in the desired manner may be used. Examples of matrix materials which are suitable for use in the practice of the present invention include: hydrophilic polymers, hydrophobic polymers and mixtures thereof which are capable of modifying the release of the compound of interest dispersed therein in vitro or in vivo: Modified-release matrix materials suitable for the practice of the present invention include but are not limited to microcrytalline cellulose, sodium carboxymethylcellulose, hydoxyalkylcelluloses such as hydroxypropylmethylcellulose (HPMC) and hydroxypropylcellulose, polyethylene oxide, alkylcelluloses such as methylcellulose and ethylcellulose, polyethylene glycol, polyvinylpyrrolidone, cellulose acteate, cellulose acetate butyrate, cellulose acteate phthalate, cellulose acteate trimellitate, polyvinylacetate phthalate, polyalkylmethacrylates, polyvinyl acetate and mixture thereof.

Several methods to affect a delayed release with non-pH dependent polymers are known to those skilled in the art. These include soluble or erodible barrier systems, enzymatically degraded barrier systems, rupturable coating systems, and plugged capsule systems among others. These systems have been thoroughly described in the literature (see "A Review of Pulsatile Drug Delivery" by Bussemer and Bodmeier in the Winter 2001 issue of American Pharmaceutical Review) and formulations and methods for their manufacture are hereby incorporated by reference.

Materials that can be used to obtain a delay in release suitable for the present invention can be, but are not limited to, polyethylene glycol (PEG) with molecular weight above 4,000 daltons (CARBOWAX®, POLYOX®), waxes such as white wax or bees wax, paraffin, acrylic acid derivatives (EUDRAGIT®), propylene glycol, and ethylcellulose.

A pH sensitive (enteric) release formulation can include the same materials as listed above with additional polymers integrated into the composition, or as coatings over the pellet or granule. The kind of materials useful for this purpose can be, but are not limited to, cellulose acetate phthalate, EUDRAGIT L®, EUDRAGIT S®, EUDRAGIT FS®, and other phthalate salts of cellulose derivatives.

A sustained release formulation can include the same materials as previously listed with additional polymers integrated into the composition, or as coatings over the pellet or granule. The kind of materials useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; EUDRAGIT R®; EUDRAGIT RS®; and Eudragit EUDRAGIT RL®; CARBOPOL®; or polyethylene glycols with molecular weights in excess of 8,000 daltons.

When it is desired to delay initiation of release of the sustained release dosage form, an appropriate coating may be used to delay initiation of the sustained release, such as a pH sensitive or a non-pH sensitive coating.

A non-pH sensitive coating for a sustained release dosage formulation can include the same materials as previously listed and/or the materials that can be used to obtain a delay in release suitable for the invention can be, but are not limited to, polyethylene glycol (PEG) with molecular weight above 4,000 daltons (CARBOWAX®, POLYOX®), waxes such as white wax or bees wax, paraffin, acrylic acid derivatives (EUDRAGIT RS®), cellulose acetate, and ethylcellulose. Preferably the materials are present in an amount just enough to provide the desired in vivo lag time and Tmax.

For local administration, the pharmaceutical compositions of the invention may also be prepared as a biodegradable controlled release polymeric matrix, for example a hydrogel, dispersion, or colloidal suspension. In a preferred embodiment, the total concentration of MASL at the local level is in the range of about 50 nM to about 2800 nM. Hydrogels are formed by incorporation of a swellable, gel-forming polymer such as those set forth above as suitable thickening agents (i.e., MC, HEC, HPC, HPMC, NaCMC, PVA, or hyaluronic acid or a salt thereof, e.g., sodium hyaluronate), except that a formulation referred to in the art as a "hydrogel" typically has a higher viscosity than a formulation referred to as a "thickened" solution or suspension.

In contrast to such preformed hydrogels, a pharmaceutical composition may also be prepared so as to form a hydrogel in situ following application to a joint or a location containing cartilage. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives, and ABA block copolymers of ethylene oxide and propylene oxide. Examples of biodegradable polymers or substances which can be used in this invention include polymers or copolymers containing polylysine, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, gelatin, collagen, hyaluronic acid, fibrin, and copolymers, or mixtures of the aforementioned materials.

The pharmaceutical compositions can also be prepared in the form of a dispersion or colloidal suspension. Preferred dispersions are liposomal, in which case the pharmaceutical composition is enclosed within "liposomes," microscopic vesicles composed of alternating aqueous compartments and lipid bilayers. Colloidal suspensions are generally formed from microparticles, i.e., from microspheres, nanospheres, microcapsules, or nanocapsules, wherein microspheres and nanospheres are generally monolithic particles of a polymer matrix in which the pharmaceutical composition is trapped, adsorbed, or otherwise contained, while with microcapsules and nanocapsules, the formulation is actually encapsulated.

The pharmaceutical composition may also be incorporated into a sterile insert that provides for controlled release of the formulation over an extended time period, generally in the range of about 12 hours to 60 days, and possibly up to 12 months or more, following implantation of the insert into or near a joint or a location containing cartilage. One type of insert is an implant in the form of a monolithic polymer matrix that gradually releases the pharmaceutical composition to or near a joint or location containing cartilage through diffusion and/or matrix degradation. With such an insert, it is preferred that the polymer be completely soluble and or biodegradable (i.e., physically or enzymatically eroded in the eye) so that removal of the insert is unnecessary. These types of inserts are well known in the art, and are typically composed of a water-swellable, gel-forming polymer such as collagen, polyvinyl alcohol, or a cellulosic polymer. Another type of insert that can be used to deliver the present formulation is a diffusional implant in which the formulation is contained in a central reservoir enclosed within a permeable polymer membrane that allows for gradual diffusion of the pharmaceutical composition out of the implant. Osmotic inserts may also be used, i.e., implants in which the pharmaceutical composition is released as a result of an increase in osmotic pressure within the implant following application to or near a joint or a location containing cartilage.

In an embodiment, the active agent, for example MASL, is released over a period of at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, or even longer.

The pharmaceutical composition may further comprise a second active agent, for example, including without limitation non-steroidal anti-inflammatory drugs (NSAIDs), corticosteroids, opiate agonists, TNF inhibitors, and disease-modifying antirheumatic drugs (DMARDs).

Examples of TNF inhibitors include without limitation infliximab (REMICADE®), adalimumab (HUMIRA®), certolizumab pegol (CIMZIA®), golimumab (SIMPONI®), and etanercept (ENBREL®).

Examples of DMARDs include without limitation chloroquine hydroxychloroquine (PLAQUENIL®), leflunomide (ARAVA®), cyclosporine (NEORAL®), sulfasalzine (AZULFIDINE®), methotrexate (RHEUMATREX®, TREXALL®), azathioprine (IMURAN®), cyclophosphamide (CYTOXAN®), minocycline, sulfasalazine, and D-penicillamine.

Examples of corticosteroids include cortisone, prednisolone, triamcinolone, flurometholone, dexamethasone, medrysone, loteprednol, fluazacort, hydrocortisone, prednisone triamcinolone, betamethasone, prednisone, methylprednisolone, triamcinolone acetonide, triamcinolone hexacatonide, paramethasone acetate, diflorasone, fluocinolone and fluocinonide, derivatives thereof, and mixtures thereof. Examples of antiviral agents include interferon gamma, zidovudine, amantadine hydrochloride, ribavirin, acyclovir, valciclovir, dideoxycytidine, and derivatives thereof. Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

It will be appreciated by persons skilled in the art that the pharmaceutical compositions of the invention may be administered locally or systemically to treat a subject suffering from an inflammatory joint disease. Routes of administration include nasal, pulmonary, buccal, parenteral (intravenous, subcutaneous, and intramuscular), and oral. Local administration is generally directed to the source and location of joint pain, and administering a biodegradable controlled release polymeric matrix in the form of a hydrogel, or implant is known in the art. In another embodiment, suitable preparation forms are, for example granules, powders, tablets, coated tablets, (micro) capsules, microparticles, syrups, emulsions, microemulsions, defined as optically isotropic thermodynamically stable systems consisting of water, oil and surfactant, liquid crystalline phases, defined as systems characterized by long-range order but short-range disorder (examples include lamellar, hexagonal and cubic phases, either water- or oil continuous), or their dispersed counterparts, gels, dispersions, suspensions, creams, aerosols, droplets or injectable solution in ampule form and also preparations with protracted release of active compounds, in whose preparation excipients, diluents, adjuvants or carriers are customarily used as described above.

The dosage required depends on the choice of the route of administration; the nature of the formulation; the nature of the patient's illness; the subject's size, weight, surface area, age, and sex; other drugs being administered; and the judgment of the clinician. Suitable dosages are in the range of 0.01-250 mg/kg. Variations in the needed dosage are to be expected in view of the variety of compounds available that may be combined and the different efficiencies of various routes of administration. Variations in these dosage levels can be adjusted using standard empirical routines for optimization as is well understood in the art that may be employed by the ordinarily skilled artisan without undue experimentation. Encapsulation of the compound in a suitable delivery vehicle (e.g., polymeric microparticles, hydrogel, or an implant) may increase the efficiency of systemic and local delivery to the area surrounding a joint.

As described herein are methods of treating joint inflammatory disease, methods of preventing joint inflammatory disease, methods of preventing the degradation of cartilage, as well as methods of screening a subject for joint inflammatory disease by administering to a subject in need thereof a pharmaceutical composition as previously described.

Another aspect of the present invention is directed to methods of reversing arthritic cartilage degeneration by factors that shift expression of $\alpha$-2,6 sialylated glycoproteins to $\alpha$-2,3 sialylated glycoproteins in chondrocytes. In such aspect, methods of treating of joint inflammatory disease including without limitation, osteoarthritis, rheumatoid arthritis, gout and pseudo-gout, ankylosing spondylitis, juvenile idiopathic arthritis, and psoriatic arthritis are described.

The above-described active agent that targets and binds to an $\alpha$-2,3-sialic acid glycoprotein, or pharmaceutical compositions comprising a selectin, mucin, galectis, lectin or antibody, can be used to treat arthritis, and prevent degradation of cartilage. Accordingly, the invention provides a method of decreasing cartilage degradation in a subject in need thereof by administering to the subject a pharmaceutical composition comprising that targets and binds to an $\alpha$-2,3-sialic acid glycoprotein and a pharmaceutically acceptable carrier in an amount effective to decrease degradation of cartilage.

In another embodiment, the invention provides a method for screening a subject for an inflammatory joint disease by administering a pharmaceutical composition as previously described, measuring the level of the detectable label present in the subject, comparing the measured level with a baseline or normalized level of a control subject that is not suffering from an inflammatory joint disease, wherein a deviation from the level of from the baseline is an indication of inflammatory joint disease. In a preferred embodiment, the deviation is caused by a modification of a sialylated expression pattern on a chondrocyte.

In another embodiment, the invention provides a method for screening the susceptibility of a subject suffering from an inflammatory joint disease to a treatment targeting PDPN expressed by a chondrocyte comprising obtaining chondrocytes from a subject, measuring the chondrocyte expression level of PDPN, administering a PDPN inhibitor to said chondrocyte, comparing the measured level with a baseline or normalized level of a control subject that is not suffering from inflammatory joint disease, wherein a deviation of the level from the baseline is an indication of inflammatory joint disease; and wherein the deviation is caused by a modification of a sialylated expression pattern on a chondrocyte expression.

The detection methods can be used to detect an agent with a detectable label in a biological sample in vitro as well as in vivo. In vitro techniques for detection of the agent include ELISAs, immunoprecipitations, immunofluorescence, EIA, RIA, flow cytometry, FISH, and Western blotting analysis. In vivo techniques for detection of the detectable agent include introducing into a subject a labeled anti-antibody or labeled lectin. For example, the antibody or lectin can be labeled with a detectable substance as described above. The presence and location of the detectable substance in a subject can be detected by standard imaging techniques.

The diagnostic methods described herein can identify subjects having, or at risk of developing arthritis. The prognostic assays described herein can be used to determine whether a subject is suitable to be administered with an agent to treat arthritis. For example, such assays can be used to determine whether a subject can be administered with the pharmaceutical compositions described above or other suitable agents to treat the arthritis.

In an embodiment, the invention provides a method of treating osteoarthritis in a subject in need thereof comprising administering to said subject a therapeutically effective amount of a pharmaceutical composition previously described. Osteoarthritis mostly affects cartilage; healthy cartilage allows bones to glide over one another. It also absorbs energy from the shock of physical movement. In osteoarthritis, the surface layer of cartilage breaks and wears away. This allows bones under the cartilage to rub together, causing pain, swelling, and loss of motion of the joint. Over time, the joint may lose its normal shape. Also, small deposits of bone—called osteophytes or bone spurs—may grow on the edges of the joint. Bits of bone or cartilage can break off and float inside the joint space. This causes more pain and damage. One aspect of the present invention is directed towards reversing or reducing the formation of such bone spurs.

In another embodiment, the invention provides a method of treating the symptoms of rheumatoid arthritis in a subject in need thereof comprising administering to said subject a therapeutically effective amount of a pharmaceutical composition previously described. Rheumatoid arthritis is an inflammatory disease that causes pain, swelling, stiffness, and loss of function in the joints. It occurs when the immune system, which normally defends the body from invading organisms, turns its attack against the membrane lining the joints. Symptoms of rheumatoid arthritis include, tender, warm, swollen joints; symmetrical pattern of affected joints; joint inflammation often affecting the wrist and finger joints closest to the hand; joint inflammation sometimes affecting other joints, including the neck, shoulders, elbows, hips, knees, ankles, and feet; fatigue, occasional fevers, a loss of energy; and pain and stiffness lasting for more than 30 minutes in the morning or after a long rest. These symptoms last for many years.

In a further embodiment, wherein osteoarthritis or RA is being treated, the baseline local level of reactive oxidative species is reduced, by as much as 1%, 5%, 7.5%, 10%, preferably 10% or more. Also, in other words, the baseline local level of ROS is reduced two fold or more from the baseline. ROS can also be determined by measuring surrogate markers that are known in the art. A deviation from the baseline may indicate a condition or disease, including arthritis. At least one aspect of the invention is to detect deviations of ROS from their baselines in patients at risk of developing an inflammatory joint disease.

In certain embodiments, the invention provides a kit for the treatment of arthritis, the prevention of cartilage degradation and/or to determine the type of therapy the subject is in need of. The kit may contain multiple doses of a pharmaceutical composition as previously described. In a preferred embodiment, the pharmaceutical composition comprises a lectin or an antibody that binds to a α-2,3-sialic acid transmembrane glycoprotein. In a most preferred embodiment the lectin is MASL. The kit may further comprise a set of instructions to perform the methods of treatment as previously described. The kit may further comprise reagents to detect cartilage degradation, reagents to detect biomarkers that reflect inflammation of the joint, reagents to detect α-2,3-sialylated glycoproteins, including PDPN, and/or determine the efficacy of the treatment. Examples of markers that reflect inflammation of the joint include without limitation, ROS, IL-6, COX2, metalloproteinase 3 (MMP3) and matrix metalloproteinase 13 (MMP13).

The following non-limiting example serves to further illustrate the invention.

EXAMPLES

Materials and Methods

Cartilage collection and processing. Human knee and femoral head articular cartilage samples were obtained from adult donors undergoing joint surgery. All donors signed an informed consent form, and the institutional Ethics Committee approved the study. In situ cartilage samples were frozen immediately in CRYOMOLD® Standard using TISSUE-TEK® O.C.T.™ compound and isopentane in liquid nitrogen and stored at −80° C. Histological samples (healthy and arthritic with radiologic diagnosis) were graded using the modified Mankin score. Samples from normal/healthy, early arthritic, and moderate grade II and III groups were selected.

Primary culture of chondrocytes. For the isolation and culture of primary chondrocytes, fresh cartilage was rinsed with saline, and cells were isolated. Cells (2.5 million) were then seeded into 162-cm$^2$ flasks, and incubated at 37° C. in 5% $CO_2$ and 100% humidity in DMEM supplemented with 100 µg/ml Primocin (Invivo Gen PRIMOCIN™) and 15% FCS (Life Technologies Gibco) until ~80-90% confluence was reached. These chondrocytes were used in experiments during the third or fourth weeks of primary culture. Cell morphology and collagen II expression was assayed to confirm cultured chondrocyte phenotype, and dedifferentiated cells were discarded.

Primary culture of synoviocytes. Synoviocytes were isolated from synovial tissue from human donors. Briefly, synovial tissue was chopped into small pieces and cultured at 5% $CO_2$ and 37° C. Primary cells attached to the 100 mm dish, and were cultured in RPMI 1640 with 20% FBS and 0.1% insulin solution.

Cell Viability assay. Cells in 96-well culture plates were treated with 0 nM, 400 nM, and 720 nM MASL (Sentrimed MASL) with and without 5 µg/ml of the ATP synthase blocker oligomycin (Sigma Aldrich) for 1 hour and 17 hours. Cytotoxicity of these drugs was evaluated by the colorimetric MTT (3-(4,5-dimethylthiazol-2-yl)-2,5-diphenyltetrazolium bromide) assay (Cell Proliferation Kit I from Roche) with a Nanoquant microplate reader (Tecan Trading AG, Switzerland) at 570 nm.

Adhesion assay. Cells were seeded onto fibrinogen-coated wells in the presence of 400 nM or 720 nM of MASL for 1 hour. Wells coated with BSA were used as negative controls. Cell adhesion was evaluated using the CYTOSELECT™ Cell Adhesion assay kit (Cell Biolabs, Inc.) and measured with a Nanoquant microplate reader (Tecan Trading AG, Switzerland) at a wavelength of 560 nm.

Cell growth and migration. Cells were grown to confluence in 24-well culture plates containing an insert which forms a 0.9 mm gap on the monolayer (Cell Biolabs, Inc. CytoSelect™ Wound Healing Assay Kit). After the insert was removed, cells were treated with 720 nM or 400 nM of MASL for 24 hours (TC28a2) or 10 days (primary chondrocytes) in DMEM supplemented with 1% FCS. Cells were imaged under an inverted light microscope (Nikon Eclipse Ti and NIS-Elements software).

Flow cytometry. ROS formation was assessed by Flow Cytometry (BD FACScalibur™, BD Bioscience) as measured by changes in the fluorescence intensity of DCF, which is the oxidation product of DCFH-DA. Briefly, cells were seeded onto 24-well plates and grown to confluence. Cells were then washed with serum free media and were cultured for 3 hours in the same medium before incubating them with DCFH-DA at 37° C. in the dark for 45 minutes. Cells were immediately treated with MASL (200, 400 or 720 nM) with or without 5 µg/ml oligomycin for 1 hour. Cells were recovered using trypsin and washed with PBS before analysing by flow cytometry.

Tissue culture. 4 mm cartilage punches were prepared from cartilage explants that were cut in the operating room immediately after surgery using a Biopsy Punch BP-40F (Kai Corporation, Japan). Punches were cultured in 48 well culture plates overnight in DMEM without serum. Medium was changed to DMEM with 0.1% FCS containing MASL and/or oligomycin, and incubated for 7 days. 400 nM of MASL was added to the medium 40 min before adding 5 µg/ml of oligomycin. Medium and drugs were replaced every 2 days. At the end of the experiments, every punch was cut in two parts; half was used for RNA isolation and the other half was frozen in CRYOMOLD® Standard and TISSUE-TEK® O.C.T. compound, and stored at −80° C. for immunohistochemistry and inmmunofluorescence assays.

Immunohistochemistry and immunofluorescence. Cells were cultured on chamber slides and fixed with 4% formaldehyde for 10 min at room temperature. Frozen cartilage sections were serially sectioned (4 µm) and processed as previously described with minor modifications. Samples were counterstained with haematoxylin/eosin or 4',6-diamidino-2-phenyindole (DAPI) (Sigma Aldrich). Anti-MMP3 antibody (MAB3369), MMP13 (MS-850-P1), and anti-Podoplanin antibody (18H5) were supplied from Merck Millipore, Thermo Fisher Scientific, and Abcam, respectively. Negative controls without primary antibody were performed to test the specificity of each antibody. Cartilage sections were stained with haematoxylin/eosin, Safranine O/Fast Green, Masson's trichrome, and Alcian Blue-PAS. Samples were analysed on an Olympus BX61 microscope using a DP71 digital camera (Olympus), and calibration and quantification of the images was performed using Analy-SIS$^D$ 5.0 software (Olympus Biosystems Hamburg, Germany).

Lectin-binding analysis. MASL was conjugated to HiLyte Fluor TR (red) to study its binding to $\alpha$-2,3-linked sialic acid modified glycoproteins on cultured cells and cartilage. Chamber slides of primary cultures or tissue sections were exposed to a solution containing 200 µg/ml conjugated MASL in PBS for 20 minutes at room temperature. Samples were washed with PBS and processed for analysis by microscopy.

Quantitative RT-PCR. Total RNA was isolated from chondrocytes using TRIZOL® reagent according to manufacturer's instructions (Invitrogen). Frozen cartilage was pulverized with a pre-chilled mortar and recovered in 1 ml of QIAZOL® lysis reagent (74804, Qiagen). Samples were incubated on ice for 5 min. 200 µl of chloroform was added to each sample, which were then vigorously agitated for 15 sec, and incubated for 3 min at room temperature. RNA was isolated using the QIACUBE® following manufacturer's instructions (Qiagen). RNA was treated with DNase (RNase-free DNase, Invitrogen) to ensure degradation of DNA in samples. A total of 1 µg of total RNA per reaction was used to generate cDNA with SUPERSCRIPT® VILO™ cDNA Synthesis Kit as instructed by the manufacturer (Invitrogen). Quantitative PCR was performed with Light-Cycler 480 SYBR Green I Master from Roche on a real-time PCR machine (LIGHTCYCLER® 480 System, Roche) and the following primers listed:

| Name | | Oligo |
|------|---|-------|
| IL-6 | F | GATGAGTACAAAAGTCCTGATCCA |
|      | R | CTGCAGCCACTGGTTCTGT |
| COX2 | F | CTTCACGCATCAGTTTTTCAAG |
|      | R | TCACCGTAAATATGATTTAAGTCCAC |
| MMP3 | F | CCCTGGGTCTCTTTCACTCA |
|      | R | GCTGACAGCATCAAAGGACA |

Statistical Analysis. Data were analyzed using the GraphPad Prism software version 5. Data are presented as mean±S.E.M. Significance of difference in the mean values was determined using the Student's t-test and Kruskal-Wallis test with Dunn's Multiple Comparison test. Significant differences are represented as $P<0.05$ and $P<0.01$. Several independent experiments were performed to guarantee reproducibility of finding Results MASL was used to investigate sialic acid modifications in chondrocytes from normal and arthritic articular cartilage. In situ analysis of joint replacement samples from surgery from patients with osteoarthritis indicate that chondrocyte glycoproteins in osteoarthritic cartilage are highly $\alpha$-2,3-sialylated compared to the normal articular cartilage. Chondrocytes in healthy cartilage showed minimal MASL binding restricted mostly to superficial zone. In contrast, cartilage explants from patients with osteoarthritis showed strong MASL binding to chondrocytes in the superficial and intermediate zones.

Expression of the α-2,3-sialylated glycoprotein PDPN receptor is induced during pathological conditions including rheumatoid arthritis. High levels of PDPN were detected in superficial and deeper zones of osteoarthritic cartilage. PDPN and MASL colocalized in human chondrocytes. The results indicate that PDPN expression can be induced in chondrocytes undergoing both osteoarthritis and rheumatoid arthritis, and that MASL can target PDPN on these cells.

MASL treatment did not affect the viability of human chondrocytes. MASL toxicity was evaluated, and MASL did not affect the adhesion, growth, or migration of primary chondrocytes, primary synoviocytes, or the established chondrocyte cell line TC28a2.

Independent of the aetiology, all cases of arthritis exhibit a notable increase in levels of reactive oxygen species (ROS) and proinflammatory cytokines. This process is especially pronounced during periods of arthritic flares, and triggers a characteristic degradation of cartilage matrix. Cells and cartilage explants were treated with the ATP synthase inhibitor oligomycin to mimic this pathological condition.

Oligomycin increased the production of α-2,3-sialylatated glycoproteins in cartilage explants as detected by MASL binding. Moreover, oligomycin treatment increased the expression of enzymes responsible for ECM degradation including matrix metalloproteinase 3 (MMP3) and matrix metalloproteinase 13 (MMP13) in primary chondrocyte cell cultures and cartilage explants. Effects of this treatment were evident after 7 days when explants showed increased ECM degradation observed by a significant increase in the size of lacunas and positive staining for MMP3 and MMP13 from lacunas to the matrix. In addition, oligomycin treatment increased ROS production in chondrocytes by over 10 fold. Although oligomycin induced ROS and metalloproteinase production leading to ECM degradation, it did not affect chondrocyte cell viability.

Protective effects of MASL on chondrocyte cell cultures was observed. Having established that oligomycin can be used to drive characteristics of arthritis, MASL was evaluated. Established (Tc28a2) and primary chondrocytes pretreated with MASL were effectively protected from ROS production in the face of oligomycin treatment as shown in FIGS. 1A-1F. 1. In addition, induction of inflammatory cytokines including IL-6 and COX2 by olygomycin was also suppressed by treatment with nanomolar MASL concentrations (FIGS. 1A-1F).

Figure 2A:
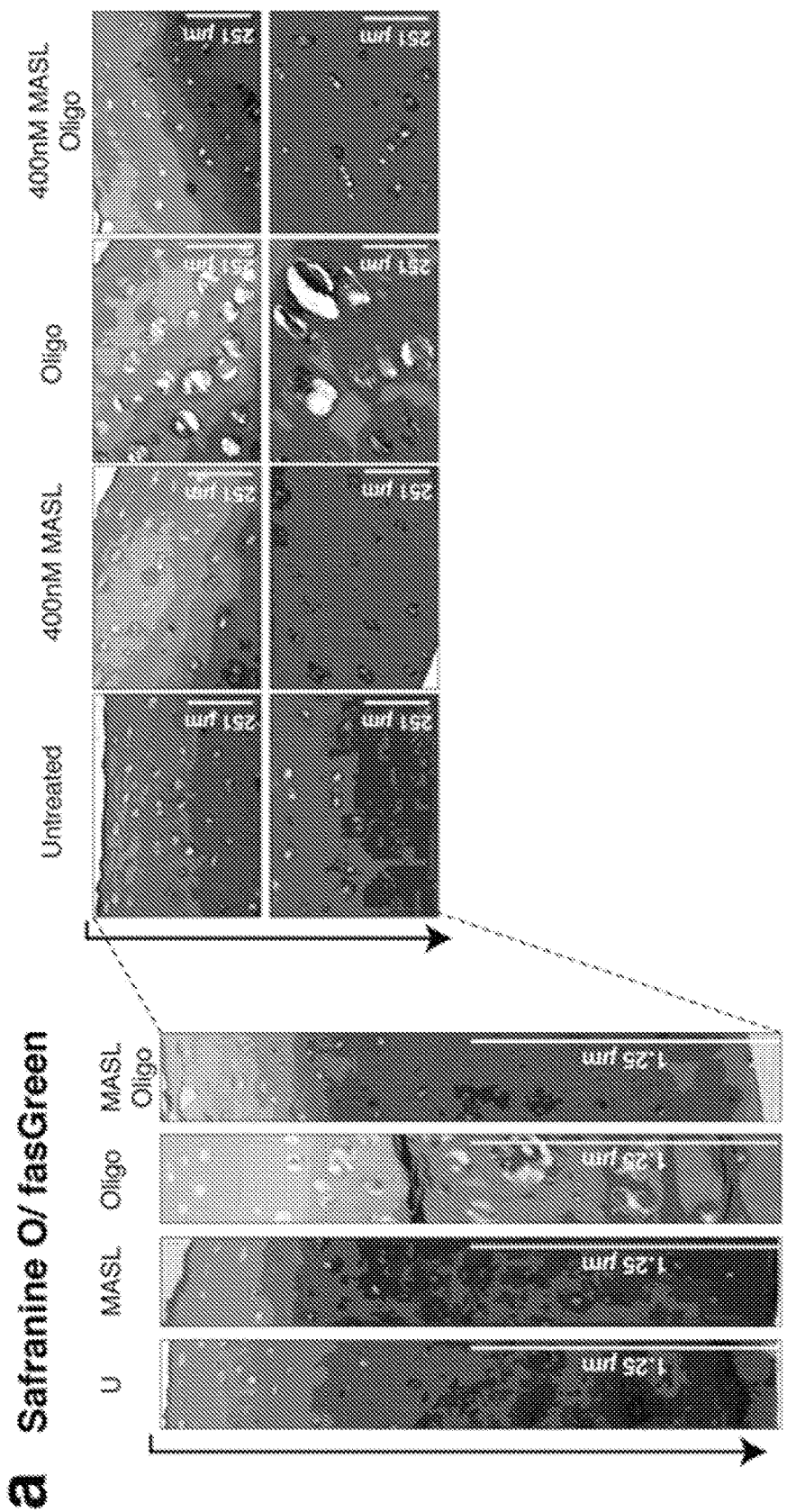
FIGS. 2A-2C are diagrams showing that MASL protects cartilage from degeneration induced by oligomycin, by depicting the expression level of COX2 and MMP3.
Figure 2B:
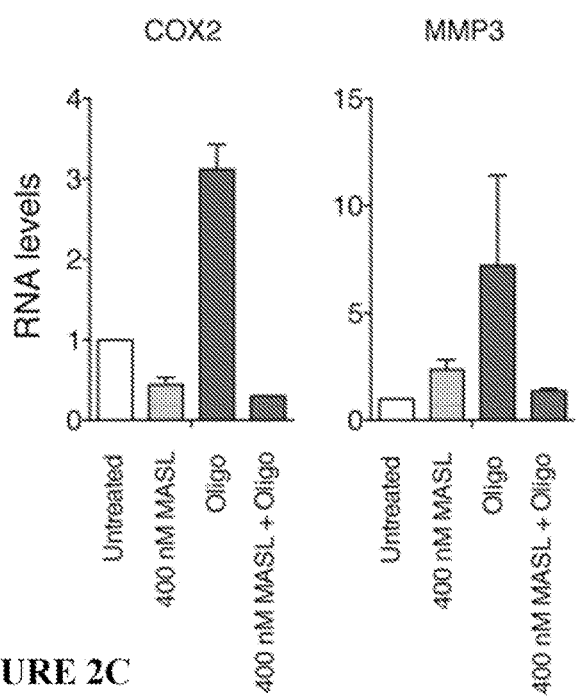
Figure 2C:
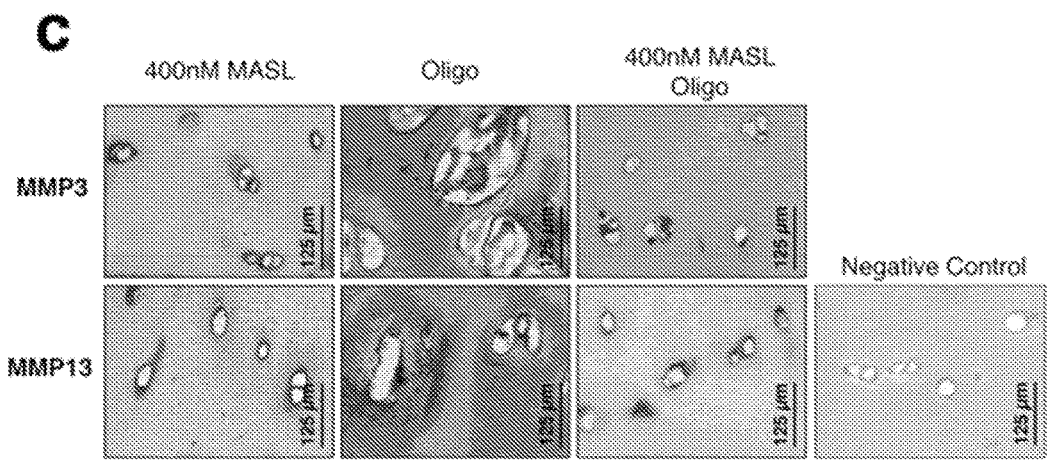

MASL prevented cartilage destruction and reduced ECM degradation detected by safranin uptake. Cartilage punches were then prepared from explants from patients with osteoarthritis. Sister punches were cultured for 7 days in medium containing oligomycin with and without MASL. Cartilage structure and proteoglycan expression were assessed by hematoxylin-eosin stain, Toluidine Blue, and uptake of Safranine O-fast green. As observed, oligomycin treatment decreased safranin uptake and disrupted the cartilage ECM as evidenced by ulcerations and increasing lacunas size. Gene expression analysis and IHC assays revealed that MASL suppressed COX2, MMP3 and MMP13 induction by oligomycin treatment (FIGS. 2A-2C).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of decreasing cartilage degradation in a subject, the method comprising administering to the subject a pharmaceutical composition comprising at least one pharmaceutically acceptable carrier and a therapeutically effective amount of an agent that binds to a α-2,3-sialic acid transmembrane glycoprotein, wherein the agent is a lectin selected from the group consisting of *Maackia* plant lectin and *Viscum* plant lectin.

2. The method of claim 1, wherein the α-2,3-sialic acid transmembrane glycoprotein is Podoplanin (PDPN).

3. The method of claim 2, wherein the PDPN is expressed by a chondrocyte.

4. The method of claim 1, wherein the *Maackia* plant is selected from the group consisting of *Maackia amurensis, Maackia australis, Maackia chekiangensis, Maackia ellipticocarpa, Maackia fauriei, Maackia floribunda, Maackia hugehesis, Maackia hwashanensis, Maackia tashiroi*, and *Maackia tenuifolia*.

5. The method of claim 4, wherein the lectin is a *Maackia amurensis* seed lectin (MASL).

6. The method of claim 1, wherein the lectin is viscumin.

7. A method of treating inflammatory joint disease in a subject, the method comprising administering to the subject a pharmaceutical composition comprising at least one pharmaceutically acceptable carrier and a therapeutically effective amount of an agent that binds to a α-2,-3-sialic acid transmembrane glycoprotein, wherein the agent is a lectin selected from the group consisting of *Maackia* plant lectin and *Viscum* plant lectin.

8. The method of claim 7, wherein the inflammatory joint disease is arthritis.

9. The method of claim 8, wherein the arthritis is osteoarthritis or rheumatoid arthritis.

10. The method of claim 7, wherein the α-2,3-sialic acid transmembrane glycoprotein is Podoplanin (PDPN).

11. The method of claim 7, wherein the *Maackia* plant is selected from the group consisting of *Maackia amurensis, Maackia australis, Maackia chekiangensis, Maackia ellipticocarpa, Maackia fauriei, Maackia floribunda, Maackia hugehesis, Maackia hwashanensis, Maackia tashiroi*, and *Maackia tenuifolia*.

12. The method of claim 11, wherein the lectin is a *Maackia amurensis* seed lectin (MASL).

13. The method of claim 12, wherein the total concentration of MASL at the local level of the joint ranges from about 50 nM to about 2800 nM.

14. The method of claim 7, wherein the administration reduces the baseline local level of reactive oxidative species (ROS) in the subject.

15. The method of claim 14, wherein the baseline local level of ROS is reduced at least 10% compared to a normal baseline of a healthy subject.

16. The method of claim 8, wherein the administration reduces the baseline local level of reactive oxidative species (ROS) in the subject.

17. The method of claim 16, wherein the baseline local level of ROS is reduced by 2 fold in the subject.

18. The method of claim 13, further comprising administering to the subject a second active agent selected from the group consisting of NSAIDs, corticosteroids, opiate agonists, TNF inhibitors, and DMARDs.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 1
gatgagtaca aaagtcctga tcca                                          24

<210> SEQ ID NO 2
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 2
ctgcagccac tggttctgt                                                19

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized
```

```
<400> SEQUENCE: 3
cttcacgcat cagtttttca ag                                            22

<210> SEQ ID NO 4
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 4
tcaccgtaaa tatgatttaa gtccac                                        26

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
ccctgggtct ctttcactca                                               20

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
gctgacagca tcaaaggaca                                               20
```